United States Patent
Liu et al.

(10) Patent No.: US 8,628,237 B1
(45) Date of Patent: Jan. 14, 2014

(54) METHOD FOR MEASURING CONTACTING THERMAL RESISTANCE OF ONE-DIMENSIONAL STRUCTURES

(71) Applicants: Tsinghua University, Beijing (CN); Hon Hai Precision Industry Co., Ltd., New Taipei (TW)

(72) Inventors: Jun-Ku Liu, Beijing (CN); Qun-qing Li, Beijing (CN); Yuan Zou, Beijing (CN); Shou-Shan Fan, Beijing (CN)

(73) Assignees: Tsinghua University, Beijing (CN); Hon Hai Precision Industry Co., Ltd., New Taipei (TW)

( * ) Notice: Subject to any disclaimer, the term of this patent is extended or adjusted under 35 U.S.C. 154(b) by 0 days.

(21) Appl. No.: 13/748,757

(22) Filed: Jan. 24, 2013

(30) Foreign Application Priority Data

Oct. 31, 2012 (CN) .......................... 2012 1 04268617

(51) Int. Cl.
| | | |
|---|---|---|
| *G01K 17/00* | (2006.01) | |
| *G01N 25/20* | (2006.01) | |
| *G01N 25/00* | (2006.01) | |
| *G01K 7/00* | (2006.01) | |
| *G01K 1/00* | (2006.01) | |
| *G01K 1/16* | (2006.01) | |
| *G01J 5/00* | (2006.01) | |

(52) U.S. Cl.
USPC .................. 374/29; 374/43; 374/45; 374/183; 374/185; 374/208; 374/120; 374/130

(58) Field of Classification Search
USPC ........ 374/29, 45, 43, 183, 185, 208, 120, 130
See application file for complete search history.

(56) References Cited

U.S. PATENT DOCUMENTS

| | | | | |
|---|---|---|---|---|
| 8,148,812 B2 * | 4/2012 | Kise | ............................... | 257/707 |
| 2008/0236804 A1 * | 10/2008 | Cola et al. | ...................... | 165/185 |
| 2009/0072137 A1 * | 3/2009 | Hunt et al. | ..................... | 250/305 |
| 2010/0066398 A1 * | 3/2010 | Ando et al. | .................... | 324/760 |
| 2010/0243227 A1 * | 9/2010 | Wu et al. | ........................ | 165/185 |
| 2010/0284002 A1 * | 11/2010 | Li et al. | .......................... | 356/301 |
| 2012/0276327 A1 * | 11/2012 | Cola et al. | ...................... | 428/119 |
| 2013/0061901 A1 * | 3/2013 | Tohei et al. | .................... | 136/205 |
| 2013/0235900 A1 * | 9/2013 | Li et al. | ........................... | 374/44 |

* cited by examiner

*Primary Examiner* — Lisa Caputo
*Assistant Examiner* — Jamel Williams
(74) *Attorney, Agent, or Firm* — Altis Law Group, Inc.

(57) ABSTRACT

A method for measuring a contacting thermal resistance of one-dimensional structures is provided. A first one-dimensional structure and A second one-dimensional structure are crossed and in contact with each other to form a suspended junction. A point P of the first one-dimensional structure is heated until the first one-dimensional structure and the second one-dimensional structure reach a thermal equilibrium. A point A and a point B are selected on the first one-dimensional structure and a point C and a point D are selected on the second one-dimensional structure, wherein the point B, the point A, the suspended junction, the point C and the point D are arranged equidistantly with a distance $\Delta x$. A temperature difference $\Delta T_j$ is calculated by the formula $\Delta T_j = \Delta T_{AC} - \Delta T_{BA} - \Delta T_{CD}$. The heat flux $Q_j$ is calculated by the formula $Q_j = 2k\Delta T_{CD}/\Delta x$. The contacting thermal resistance $R_j$ is calculated by the formula $R_j = \Delta T_j/Q_j$.

15 Claims, 5 Drawing Sheets

METHOD FOR MEASURING CONTACTING THERMAL RESISTANCE OF ONE-DIMENSIONAL STRUCTURES

CROSS-REFERENCE TO RELATED APPLICATIONS

This application claims all benefits accruing under 35 U.S.C. §119 from China Patent Applications: Application No. 201210426861.7, filed on Oct. 31, 2012 in the China Intellectual Property Office, disclosures of which are incorporated herein by references. This application is related to applications entitled, "THERMAL CONDUCTIVITY MEASUREMENT APPARATUS FOR ONE-DIMENSIONAL MATERIAL AND MEASUREMENT METHOD", filed on Nov. 17, 2009 with U.S. patent application Ser. No. 12/620,073.

BACKGROUND

1. Technical Field

The present disclosure relates to methods for measuring contacting thermal resistance of one-dimensional structures.

2. Description of Related Art

Thermal resistance is an important parameter which reflects a material's ability to resist heat transfer. Contacting thermal resistance is widely used to reflect the heat transfer properties of the contacting surface between two objects in contact with each other. The calculation of contacting thermal resistance between a first object and a second object satisfies the formula below:

$$R_j = \frac{\Delta T_j}{Q_j}$$

where, the $R_j$ represents the contacting thermal resistance between the first object and the second object, $\Delta T_j$ represents a temperature difference near the contacting surface between the first object and the second object, $Q_j$ represents a heat flux flowing from the first object to the second object through the contacting surface.

Therefore, how to exactly measure the contacting thermal resistance between two objects is important for the application of the material. However, when the objects needed to be measured are one-dimensional structures, such as nanowires or carbon nanotubes, it is more difficult to measure the contacting thermal resistance. One reason is that measuring instruments are large compared to the areas of structures to be measured and so immediately affect the temperature of the structure when contact is made during measurement.

What is needed, therefore, is to provide a method which can accurately measure the contacting thermal resistance of one-dimensional structures.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

References will now be made to the drawings to describe, in detail, various embodiments of the present methods for measuring the contacting thermal resistance of one-dimensional structures.

Figure 1:
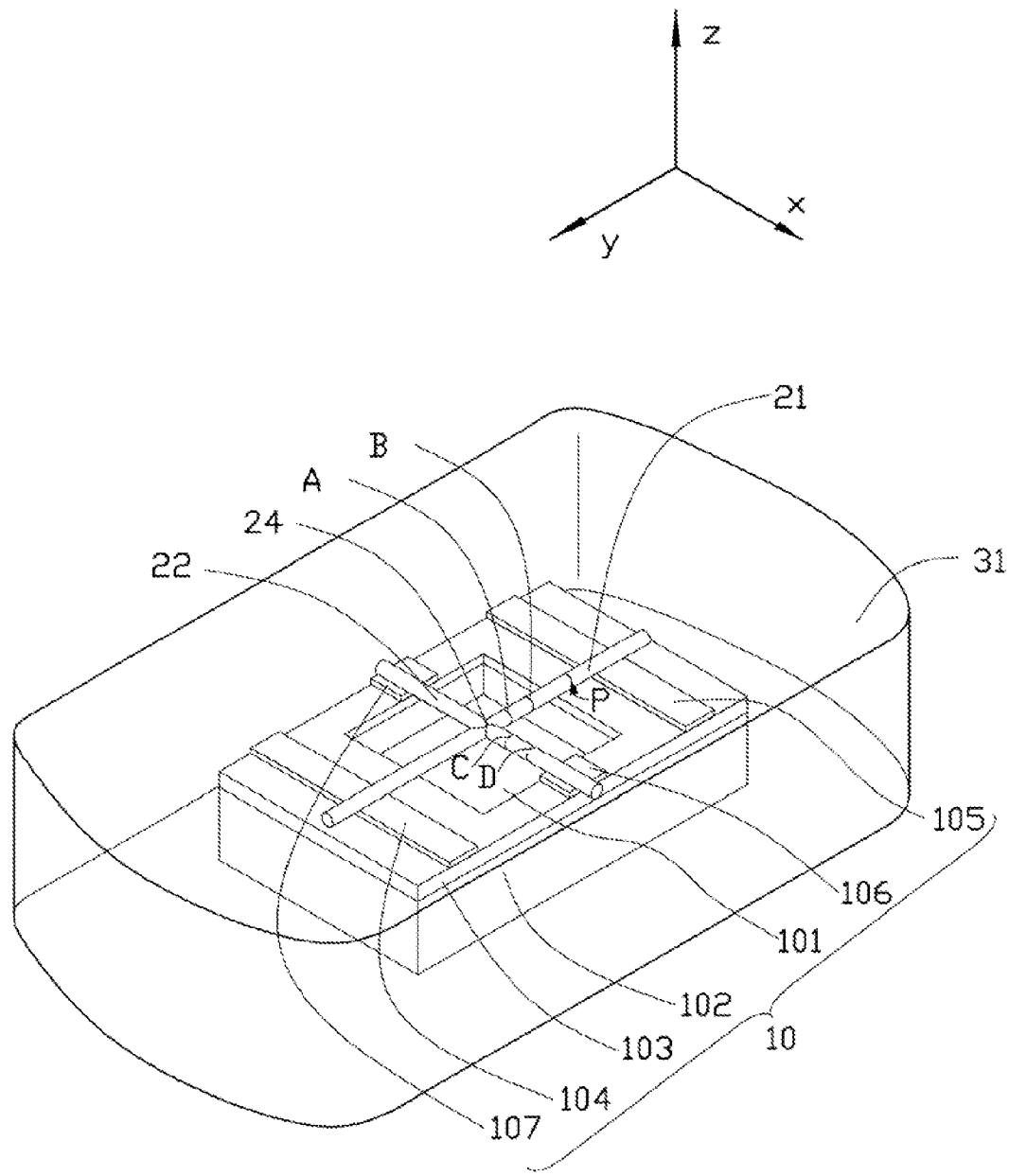
FIG. 1 is a schematic view of one embodiment of a method for measuring the contacting thermal resistance of one-dimensional structures.

Referring to FIG. 1, a method for measuring the contacting thermal resistance of one-dimensional structures of one embodiment includes the following steps:

step (S10), providing a first one-dimensional structure 21 and a second one-dimensional structure 22, wherein the first one-dimensional structure 21 and the second one-dimensional structure 22 have the same material and are crossed and in contact with each other to form a suspended junction 24;

step (S20), heating a point P spaced from the suspended junction 24 of the first one-dimensional structure 21 until the first one-dimensional structure 21 and the second one-dimensional structure 22 reach a thermal equilibrium;

step (S30), selecting a point A and a point B on the first one-dimensional structure 21 on the same side of the suspended junction 24, selecting a point C and a point D on the second one-dimensional structure 22 on the same side of the suspended junction 24, detecting and calculating a first frequency difference $\Delta Y_{AC}$ of the Raman spectrum characteristic peaks between the point A and the point C, detecting and calculating a second frequency difference $\Delta Y_{BA}$ of the Raman spectrum characteristic peaks between the point B and the point A, and detecting and calculating a third frequency difference $\Delta Y_{CD}$ of the Raman spectrum characteristic peaks between the point C and the point D, wherein the point B, the point A, the suspended junction 24, the point C and the point D are arranged equidistantly with a distance $\Delta x$;

step (S40), calculating a first temperature difference $\Delta T_{AC}$ between the point A and the point C, calculating a second temperature difference $\Delta T_{BA}$ between the point B and the point A, calculating a third temperature difference $\Delta T_{CD}$ between the point C and the point D by the formula $\Delta T = \Delta Y/a$, wherein the $\Delta T$ represents the temperature difference between two spaced points, and the $\Delta Y$ represents the frequency difference between two spaced points, and 'a' is constant;

step (S50), calculating a fourth temperature difference $\Delta T_j$ between the first one-dimensional structure 21 and the second one-dimensional structure 22 at a place near the suspended junction 24 by the formula $\Delta T_j = \Delta T_{AC} - \Delta T_{BA} - \Delta T_{CD}$;

step (S60), calculating a heat flux $Q_j$ by the formula $Q_j=2k\Delta T_{CD}/\Delta x$, wherein the $Q_j$ represents the heat flux flowing from the first one-dimensional structure 21 to the second one-dimensional structure 22 through the suspended junction 24, the k represents the thermal conductivity of the first one-dimensional structure 21 and the second one-dimensional structure 22; and step (S70), calculating a contacting thermal resistance $R_j$ by the formula $R_j=\Delta T_j/Q_j$, wherein the $R_j$ represents the contacting thermal resistance between the first one-dimensional structure 21 and the second one-dimensional structure 22 at the suspended junction 24.

In step (S10), a first measurement apparatus 10 is provided. The first measurement apparatus 10 includes a substrate 102 defining a recess 101, an insulative layer 103, a first electrode 104, a second electrode 105, a third electrode 106 and a fourth electrode 107 as shown in FIG. 1. The insulative layer 103 is located on the substrate 102. The insulative layer 103 defines an opening aligned with the recess 101. The first electrode 104, the second electrode 105, the third electrode 106 and the fourth electrode 107 are located on the insulative layer 103. The first electrode 104 and the second electrode 105 are located on opposite two sides of the recess 101 along a Y direction. The third electrode 106 and the fourth electrode 107 are located on opposite two sides of the recess 101 along an X direction.

The first one-dimensional structure 21 has a first end attached on the first electrode 104, a second end attached on the second electrode 105, and a first center portion suspended through the recess 101. The second one-dimensional structure 22 has a third end attached on the third electrode 106, a fourth end attached on the fourth electrode 107, and a second center portion suspended through the recess 101. The suspended first center portion of the first one-dimensional structure 21 and the suspended second center portion of the second one-dimensional structure 22 are crossed and in contact with each other to form the suspended junction 24. Thus, the suspended junction 24 is suspended above the recess 101. An angle between the first extending direction of the first one-dimensional structure 21 and the second extending direction of the second one-dimensional structure 22 is greater than 0 degrees and less than or equal to 90 degrees. In one embodiment, the angle is about 90 degrees. The first extending direction of the first one-dimensional structure 21 is defined as the Y direction and the second extending direction of the second one-dimensional structure 22 is defined as the X direction.

The first one-dimensional structure 21 and the second one-dimensional structure 22 are the same one-dimensional materials with an effective diameter in nanometer scales or micrometer scales. The term "effective diameter" means the maximum length of the cross-section of each of the one-dimensional materials. When the effective diameter of the one-dimensional materials is in a range from about 0.5 nanometers to about 100 nanometers, the one-dimensional materials are named as one-dimensional nanomaterials. The one-dimensional nanomaterials can be nanotubes, nanorods, nanowires, nanofibers, or nanoribbons. In one embodiment, both the first one-dimensional structure 21 and the second one-dimensional structure 22 are single wall carbon nanotubes. The area of the contacting surface at the suspended junction 24 of the two single wall carbon nanotubes is speculated as the same as the area of the cross-section of the single wall carbon nanotube.

In one embodiment, the method for making the suspended junction 24 includes following substeps of:

step (S101), placing a silicon substrate (not shown) having a silicon dioxide layer thereon near the first electrode 104, wherein the first electrode 104 is located between the silicon substrate and the second electrode 105;

step (S102), laying a carbon nanotube film on the silicon dioxide layer, wherein the carbon nanotube film is drawn from a carbon nanotube array and includes a plurality of carbon nanotubes joined end to end by van der Waals attractive force between and substantially arranged along the same direction;

step (S103), dropping a ferric chloride solution with a concentration of $10^{-5}$-$10^{-6}$ mol/liter on the carbon nanotube film, and placing the first measurement apparatus 10 with the carbon nanotube film thereon into a reaction room;

step (S104), introducing a mixture gas of hydrogen gas and helium the gas into the reaction room, and heating the ferric chloride solution to a temperature of 950° C. so that a catalyst gas is formed, wherein the flow rate of the mixture gas is in a rang from about 60 sccm to about 200 sccm;

step (S105), introducing source gas of hydrogen gas and methane gas into the reaction room along a direction from the first electrode 104 to the second electrode 105 to grow a first single wall carbon nanotube, wherein the first single wall carbon nanotube grow from the carbon nanotube film, float across the recess 101 along the source gas flow, and then fall down on the first electrode 104 and the second electrode 105, the first single wall carbon nanotube is used as the first one-dimensional structure 21; and step (S106), repeating step (S101) to step (S105) to form a second single wall carbon nanotube on the third electrode 106 and the fourth electrode 107, wherein the second single wall carbon nanotube is crossed with the first single wall carbon nanotube and used as the second one-dimensional structure 22.

Alternatively, the first one-dimensional structure 21 and the second one-dimensional structure 22 can be formed by placing two single wall carbon nanotubes under a scanning electron microscopy (SEM).

In step (S20), the heating method is not limited as long as the first one-dimensional structure 21 can be heated partially. The heating process should be maintained until the measurement is finished. In one embodiment, the first one-dimensional structure 21 is heated by a laser beam and the heated point P is on the suspended first center portion of the first one-dimensional structure 21. The distance between the point P and the suspended junction 24 is about 100 micrometers. After heating, the heat flows from the point P to the suspended junction 24 and then flows from the suspended junction 24 to the second one-dimensional structure 22 until the first one-dimensional structure 21 and the second one-dimensional structure 22 reach thermal equilibrium. The term "thermal equilibrium" means the temperatures on the each point of the first one-dimensional structure 21 and the second one-dimensional structure 22 are stable and unchanged. After thermal equilibrium, the temperature of the point P is the highest, and the temperature of the suspended junction 24 is lower than the temperature of the point P. The temperature of the second one-dimensional structure 22 gradually gets down along a direction away from the suspended junction 24.

In step (S30), the first measurement apparatus 10 with the first one-dimensional structure 21 and the second one-dimensional structure 22 are located in a vacuum chamber 31. A Raman spectrometer is used to detect the frequency Y of the Raman spectrum characteristic peak of the point B, the point A, the point C and the point D. The point B and the point A are located between the suspended junction 24 and the point P. The $\Delta x$ can be in a range from about 10 micrometers to about 100 micrometers. In one embodiment, the $\Delta x$ can be about 20 micrometers. Because the Raman laser has a spatial resolution of about 1 micrometer, the Raman spectrometer can detect the temperature of any point on the suspended portions of the first one-dimensional structure 21 and the second one-dimensional structure 22. Different materials have different Raman spectrum characteristic peaks. In the present embodiment, the first one-dimensional structure 21 and the second one-dimensional structure 22 are two single wall carbon nanotubes with peak G as the characteristic peak.

In step (S40), according to the formula Y=aT+b, the temperature difference can be calculated by the formula $\Delta T=\Delta Y/a$, wherein the $\Delta T$ represents the temperature difference between two spaced points, and the $\Delta Y$ represents the frequency difference between two spaced points.

In one embodiment, the first one-dimensional structure 21 and the second one-dimensional structure 22 are two single wall carbon nanotubes, and the formula Y=aT+b of the single wall carbon nanotube can be determined by following substeps:

step (S401), providing a support defining a groove, and placing the single wall carbon nanotube on the support so that the single wall carbon nanotube has at least one portion suspended through the groove;

step (S402), placing the support with the single wall carbon nanotube thereon onto a temperature adjusting device in a vacuum chamber, wherein the temperature of the single wall carbon nanotube can be controlled by the temperature adjusting device;

step (S403), detecting the frequency of the Raman spectrum characteristic peak of the single wall carbon nanotube at different temperatures using a Raman spectrometer, wherein the temperature of the single wall carbon nanotube is adjusted by the temperature adjusting device; and step (S404), fitting the data of the frequency of the Raman spectrum characteristic peak and temperature to obtain the formula Y=aT+b.

In step (S402), the vacuum chamber can be a quartz tube or a stainless steel chamber with a quartz window. The pressure of the vacuum chamber can be lower than $10^{-4}$ Torr. Thus, the heat conduction through the surrounding air is negligible.

Figure 2:
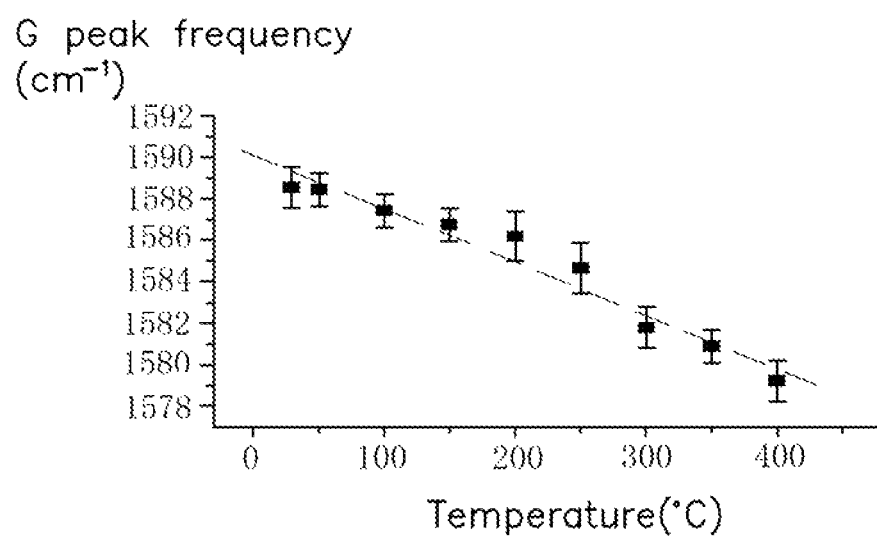
FIG. 2 shows a relationship between G peak frequencies of Raman spectrum and various temperatures of one embodiment of a single wall carbon nanotube.

In step (S403), the frequency of the Raman spectrum characteristic peak of the single wall carbon nanotube at each temperature is detected for several times and obtained by calculating an average value. The relationship between the frequencies of Raman spectrum G peak and various temperatures of the single wall carbon nanotube is shown in FIG. 2.

In step (S404), the fitting can be mathematical means such as linear regression, nonlinear regression or spline fitting. The fitting can be performed by Mathematical software such as Matlab. In one embodiment, a line is obtained by linear fitting the data as shown in FIG. 2, wherein a=−0.0257 cm$^{-1}$/K.

In step (S50), because both the first one-dimensional structure 21 and the second one-dimensional structure 22 have the same heat flux in each unit distance, both the first one-dimensional structure 21 and the second one-dimensional structure 22 have the same temperature gradient in each unit distance according to the Fourier's law of heat conduction. In one embodiment, because the heat flux between the point B and the point A is the same as the heat flux between the point A and the suspended junction 24, the temperature difference between the point B and the point A is the same as the temperature difference between the point A and the suspended junction 24. Also, the temperature difference between the suspended junction 24 and the point C is the same as the temperature difference between the point C and the point D. Thus, the fourth temperature difference $\Delta T_j$ between the first one-dimensional structure 21 and the second one-dimensional structure 22 at a place near the suspended junction 24 satisfies the formula:

$$\Delta T_j = \Delta T_{AC} - \Delta T_{BA} - \Delta T_{CD}$$

wherein the $\Delta T_j$ represents the fourth temperature difference between the first one-dimensional structure 21 and the second one-dimensional structure 22 at a place near the suspended junction 24, the $\Delta T_{AC}$ represents the first temperature difference between the point A and the point C, the $\Delta T_{BA}$ represents the second temperature difference between the point B and the point A, the $\Delta T_{CD}$ represents the third temperature difference between the point C and the point D.

In step (S60), because the heat flows from the first one-dimensional structure 21 to the second one-dimensional structure 22 through the suspended junction 24, the heat flux $Q_j$ at the suspended junction 24 satisfies the formula (1):

$$Q_j = 2 Q_{CD}$$

wherein the $Q_j$ represents the heat flux from the first one-dimensional structure 21 to the second one-dimensional structure 22 through the suspended junction 24, the $Q_{CD}$ represents the heat flux from the point C to the point D according to the Fourier's law of heat conduction.

The heat flux $Q_{CD}$ from the point C to the point D satisfies the formula (2):

$$Q_{CD} = k \Delta T_{CD} / \Delta x$$

wherein the $Q_{CD}$ represents the heat flux from the point C to the point D, the k represents the thermal conductivity of the first one-dimensional structure 21 and the second one-dimensional structure 22, the $\Delta T_{CD}$ represents the third temperature difference between the point C and the point D, and the $\Delta x$ represents the distance between the point C and the point D.

Figure 3:
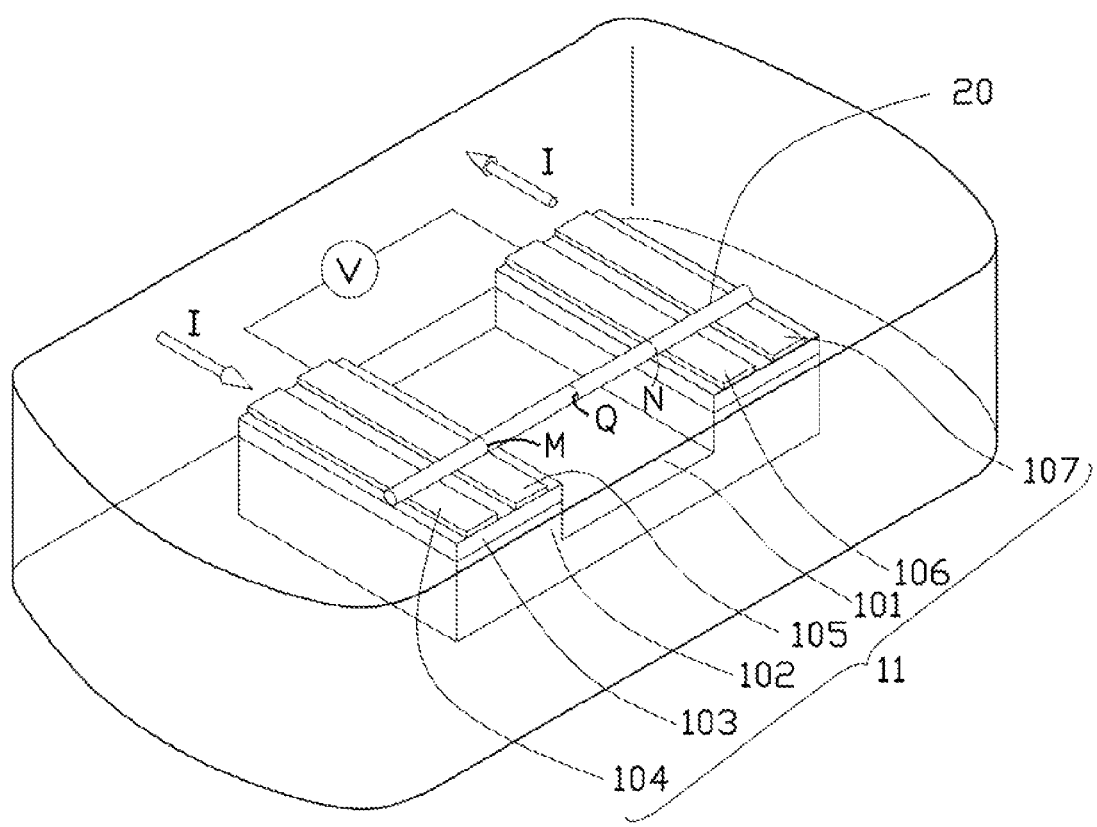
FIG. 3 is a schematic view of one embodiment of a method for obtaining the thermal conductivity.

According to the formula (1) and the formula (2), the heat flux $Q_j$ at the suspended junction 24 can be calculated by formula (3): $Q_j = 2 k \Delta T_{CD} / \Delta x$ In one embodiment, as shown in FIG. 3, the thermal conductivity k can be determined by following substeps:

step (S601), providing a second measurement apparatus 11, the second measurement apparatus 11 includes a substrate 102 defining a recess 101, an insulative layer 103, a first electrode 104, a second electrode 105, a third electrode 106 and a fourth electrode 107, wherein the first electrode 104, the second electrode 105, the third electrode 106 and the fourth electrode 107 are parallel with and spaced from each other;

step (S602), placing a third one-dimensional structure 20 on the second measurement apparatus 11, wherein the third one-dimensional structure 20 has a first portion attached on the first electrode 104 and the second electrode 105, a second portion suspended through the recess 101, and a third portion attached on the third electrode 106 and the fourth electrode 107;

step (S603), obtaining a length $\Delta L$ of the suspended second portion of the third one-dimensional structure 20 and a cross sectional area S of the third one-dimensional structure 20;

step (S604), applying a constant electric current to the third one-dimensional structure 20 by supplying a constant voltage between the first electrode 104 and the fourth electrode 107 to heat the third one-dimensional structure 20 until a thermal equilibrium is reached;

step (S605), selecting a first end point M, a center point Q and a second end point N on the suspended second portion of the third one-dimensional structure 20, detecting the frequency of the Raman spectrum characteristic peak of the first end point M, the center point Q and the second end point N, and calculating the frequency difference $\Delta Y_Q$ of the Raman spectrum characteristic peak between the first end point M and the center point Q;

step (S606), calculating the temperature difference $\Delta T_Q$ between the first end point M and the center point Q by a formula $\Delta T_Q = \Delta Y_Q/a$;

step (S607), detecting the voltage U between the first end point M and the second end point N and the electric current I flowing through the third one-dimensional structure 20, and calculating the power P by a formula P=UI; and step (S608), calculating the thermal conductivity k of the third one-dimensional structure 20 by a formula $$k = \frac{P\Delta L}{S\Delta T_Q}.$$

In step (S601), the first electrode 104 and the second electrode 105 are located on the same side of the recess 101, and the third electrode 106 and the fourth electrode 107 are located on the other same side of the recess 101.

In step (S602), the third one-dimensional structure 20 is the same as first one-dimensional structure 21 and the second one-dimensional structure 22. In one embodiment, the third one-dimensional structure 20 is a single wall carbon nanotube.

In step (S603), the third one-dimensional structure 20 is a single wall carbon nanotube in one embodiment, and the cross sectional area S can be calculated by the formula $S=\pi(2R-b)b$, wherein the R represents the outer diameter of the single wall carbon nanotube, the 'b' represents the wall thickness of the single wall carbon nanotube, and b=0.34 nanometers.

Figure 4:
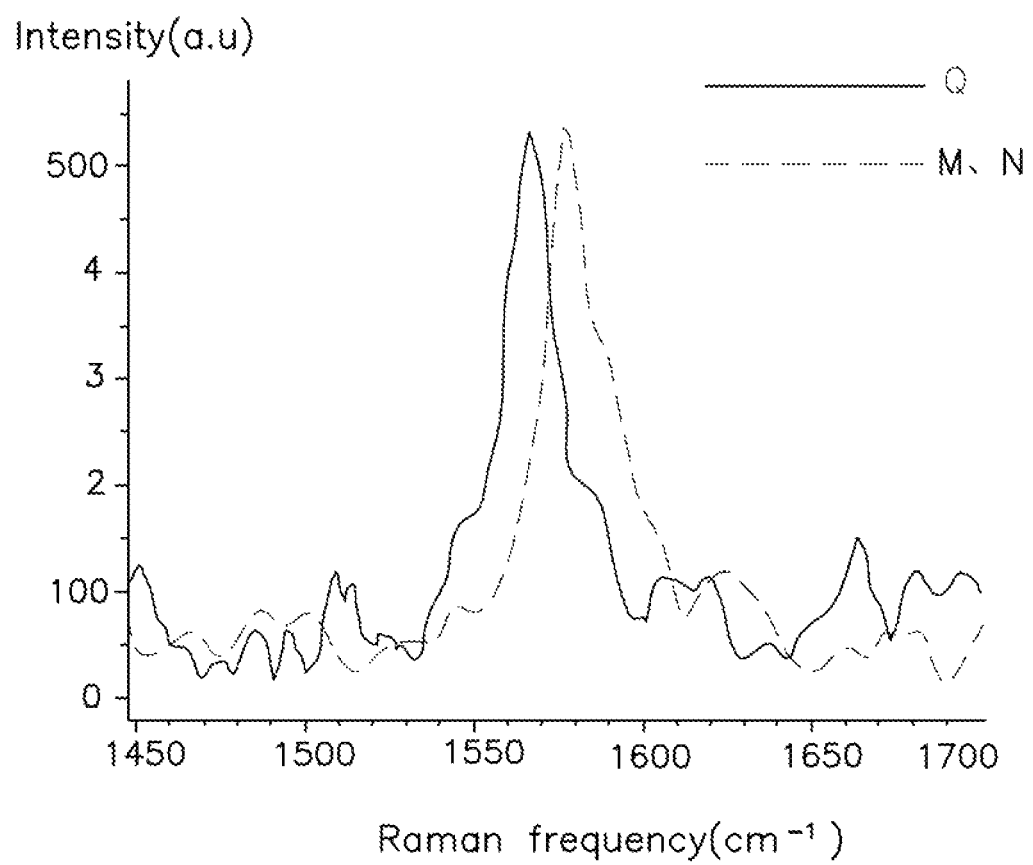
FIG. 4 shows a Raman spectrum of one embodiment of a center and an end of a suspended portion of a single wall carbon nanotube.

In step (S605), the Raman spectrum of the center point Q and the first end point M of the suspended portion of the single wall carbon nanotube is shown in FIG. 4.

The above method for obtaining the thermal conductivity k is taught by US20100284002A1 to Li et al. filed on Nov. 17, 2009 with U.S. patent application Ser. No. 12/620,073.

In step (S70), the contacting thermal resistance $R_j$ is calculated by the formula $$R_j = \Delta T_j/Q_j$$

wherein the $R_j$ represents the contacting thermal resistance between the first one-dimensional structure 21 and the second one-dimensional structure 22 at the suspended junction 24, the $\Delta T_j$ represents the fourth temperature difference between the first one-dimensional structure 21 and the second one-dimensional structure 22 at a place near the suspended junction 24, and the $Q_j$ represents the heat flux from the first one-dimensional structure 21 to the second one-dimensional structure 22 through the suspended junction 24.

Figure 5:
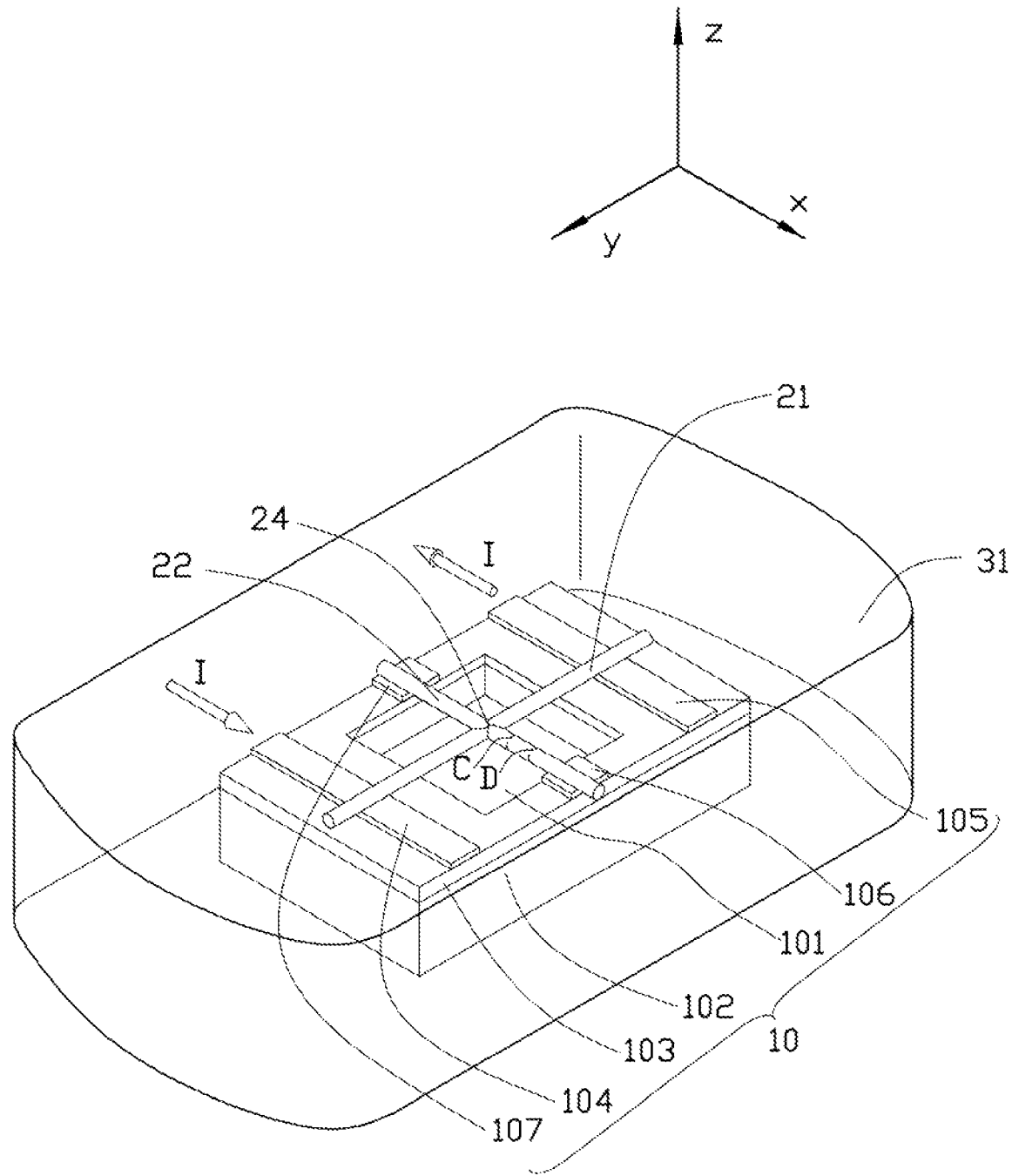
FIG. 5 is a schematic view of another embodiment of a method for measuring the contacting thermal resistance of one-dimensional structures.

Referring to FIG. 5, a method for measuring the contacting thermal resistance of one-dimensional structures of another embodiment includes the following steps:

step (S11), providing a first one-dimensional structure 21 and a second one-dimensional structure 22 both have the same material, wherein the first one-dimensional structure 21 and the second one-dimensional structure 22 are crossed and in contact with each other to form a suspended junction 24;

step (S21), applying a constant electric current to the first one-dimensional structure 21 to heat the first one-dimensional structure 21 and the second one-dimensional structure 22 until the first one-dimensional structure 21 and the second one-dimensional structure 22 reach a thermal equilibrium;

step (S31), selecting a point C and a point D on the second one-dimensional structure 22 on the same side of the suspended junction 24, detecting and calculating a fifth frequency difference $\Delta Y_{OC}$ of the Raman spectrum characteristic peaks between the suspended junction 24 and the point C, and detecting and calculating the third frequency difference $\Delta Y_{CD}$ of the Raman spectrum characteristic peaks between the point C and the point D, wherein the suspended junction 24, the point C and the point D are arranged equidistantly with a distance $\Delta x$;

step (S41), calculating a fifth temperature difference $\Delta T_{OC}$ between the suspended junction 24 and the point C, and calculating the third temperature difference $\Delta T_{CD}$ between the point C and the point D by the formula $\Delta T = \Delta Y/a$, wherein the $\Delta T$ represents the temperature difference between two spaced points, and the $\Delta Y$ represents the frequency difference between two spaced points, and 'a' is constant;

step (S51), calculating a fourth temperature difference $\Delta T_j$ between the first one-dimensional structure 21 and the second one-dimensional structure 22 at a place near the suspended junction 24 by the formula $\Delta T_j = \Delta T_{OC} - \Delta T_{CD}$;

step (S61), calculating a heat flux $Q_j$ by the formula $Q_j = 2k\Delta T_{CD}/\Delta x$, wherein the $Q_j$ represents the heat flux flowing from the first one-dimensional structure 21 to the second one-dimensional structure 22 through the suspended junction 24, the k represents the thermal conductivity of the first one-dimensional structure 21 and the second one-dimensional structure 22; and step (S71), calculating a contacting thermal resistance $R_j$ by the formula $R_j = \Delta T_j/Q_j$, wherein the $R_j$ represents the contacting thermal resistance between the first one-dimensional structure 21 and the second one-dimensional structure 22 at the suspended junction 24.

The methods for measuring the contacting thermal resistance of FIG. 1 and FIG. 5 are similar except that in step (S21), the first one-dimensional structure 21 and the second one-dimensional structure 22 are heated by applying a constant electric current to the first one-dimensional structure 21, and in step (S51), the fourth temperature difference $\Delta T_j$ is calculated according to the fifth temperature difference $\Delta T_{OC}$ between the suspended junction 24 and the point C and the third temperature difference $\Delta T_{CD}$ between the point C and the point D.

In step (S21), a constant voltage is supplied between the first electrode 104 and the second electrode 105. In one embodiment, the constant electric current is 0.2 microampere. After heating, the heat flows from the first one-dimensional structure 21 to the second one-dimensional structure 22 through the suspended junction 24 until the first one-dimensional structure 21 and the second one-dimensional structure 22 reach thermal equilibrium. After thermal equilibrium, the temperature of the second one-dimensional structure 22 gradually gets down along a direction away from the suspended junction 24.

In step (S51), the fourth temperature difference $\Delta T_j$ between the first one-dimensional structure 21 and the second one-dimensional structure 22 at a place near the suspended junction 24 is calculated by the formula:

$$\Delta T_j = \Delta T_{OC} - \Delta T_{CD}$$

wherein the $\Delta T_j$ represents the fourth temperature difference between the first one-dimensional structure 21 and the second one-dimensional structure 22 at a place near the suspended junction 24, the $\Delta T_{OC}$ represents the first temperature difference between the suspended junction 24 and the point C, the $\Delta T_{CD}$ represents the third temperature difference between the point C and the point D.

The methods for measuring the contacting thermal resistance of one-dimensional structures above can avoid a contact between the one-dimensional structures and the probe of the temperature detecting device. Thus, the contacting thermal resistance will not be influenced by the probe f the temperature detecting device and the measurement is simple and precise.

Depending on the embodiment, certain of the steps of methods described may be removed, others may be added, and the sequence of steps may be altered. It is also to be understood that the description and the claims drawn to a method may include some indication in reference to certain steps. However, the indication used is only to be viewed for identification purposes and not as a suggestion as to an order for the steps.

What is claimed is:

1. A method for measuring a contacting thermal resistance of one-dimensional structures, the method comprising:

making a first one-dimensional structure and a second one-dimensional structure so that the first one-dimensional structure and the second one-dimensional structure are crossed and in contact with each other to form a suspended junction, wherein the first one-dimensional structure and the second one-dimensional structure are the same material;

heating a point P of the first one-dimensional structure until the first one-dimensional structure and the second one-dimensional structure reach a thermal equilibrium, wherein the point P is spaced from the suspended junction;

selecting a point A and a point B on the first one-dimensional structure on the same side of the suspended junction, selecting a point C and a point D on the second one-dimensional structure on the same side of the suspended junction, detecting and calculating a first frequency difference $\Delta Y_{AC}$ of Raman spectrum characteristic peaks between the point A and the point C, detecting and calculating a second frequency difference $\Delta Y_{BA}$ of Raman spectrum characteristic peaks between the point B and the point A, and detecting and calculating a third frequency difference $\Delta Y_{CD}$ of Raman spectrum characteristic peaks between the point C and the point D, wherein the point B, the point A, the suspended junction, the point C and the point D are arranged equidistantly with a distance $\Delta x$;

calculating a first temperature difference $\Delta T_{AC}$ between the point A and the point C, calculating a second temperature difference $\Delta T_{BA}$ between the point B and the point A, calculating a third temperature difference $\Delta T_{CD}$ between the point C and the point D by a formula $\Delta T = \Delta Y/a$, wherein the $\Delta T$ represents a temperature difference between two spaced points and the $\Delta Y$ represents a frequency difference between the two spaced points, and 'a' is constant;

calculating a fourth temperature difference $\Delta T_j$ between the first one-dimensional structure and the second one-dimensional structure at the suspended junction by a formula $\Delta T_j = \Delta T_{AC} - \Delta T_{BA} - \Delta T_{CD}$;

calculating a heat flux $Q_j$ by a formula $Q_j = 2k\Delta T_{CD}/\Delta x$, wherein the $Q_j$ represents the heat flux flowing from the first one-dimensional structure to the second one-dimensional structure through the suspended junction, and the k represents a thermal conductivity of the first one-dimensional structure; and calculating a contacting thermal resistance $R_j$ by a formula $R_j = \Delta T_j/Q_j$, wherein the $R_j$ represents the contacting thermal resistance between the first one-dimensional structure and the second one-dimensional structure at the suspended junction.

2. The method of claim 1, wherein both the first one-dimensional structure and the second one-dimensional structure have an effective diameters in a range from about 0.5 nanometers to about 100 nanometers.

3. The method of claim 2, wherein both the first one-dimensional structure and the second one-dimensional structure are nanotubes, nanorods, nanowires, nanofibers, or nanoribbons.

4. The method of claim 3, wherein the first one-dimensional structure and the second one-dimensional structure are two single wall carbon nanotubes.

5. The method of claim 1, wherein the heating the point P of the first one-dimensional structure comprises heating the point P by a laser beam.

6. The method of claim 1, wherein the point P is on a suspended portion of the first one-dimensional structure and spaced from the suspended junction.

7. The method of claim 6, wherein a distance between the point P and the suspended junction is about 100 micrometers.

8. The method of claim 6, wherein the point B and the point A are located between the suspended junction and the point P.

9. The method of claim 1, wherein the $\Delta x$ is in a range from about 10 micrometers to about 100 micrometers.

10. The method of claim 1, wherein the formula $\Delta T = \Delta Y/a$ is obtained according to a formula $Y = aT + b$, wherein the Y represents a frequency of Raman spectrum characteristic peak of the first one-dimensional structure, T represents a temperature of the first one-dimensional structure, and 'b' is constant.

11. The method of claim 10, wherein the first one-dimensional structure is a single wall carbon nanotube with a peak G as the Raman spectrum characteristic peak, and the formula $Y = aT + b$ is determined by following substeps:

placing the single wall carbon nanotube on a support defining a groove so that the single wall carbon nanotube has a portion suspended through the groove;

detecting frequencies of peaks G of the single wall carbon nanotube at different temperatures; and fitting detected data of the frequencies of peaks G and the different temperatures.

12. A method for measuring a contacting thermal resistance of one-dimensional structures, the method comprising:

making a first one-dimensional structure and a second one-dimensional structure so that the first one-dimensional structure and the second one-dimensional structure are crossed and in contact with each other to form a suspended junction, wherein the first one-dimensional structure and the second one-dimensional structure are the same material;

applying a constant electric current to the first one-dimensional structure to heat the first one-dimensional structure and the second one-dimensional structure until the first one-dimensional structure and the second one-dimensional structure reach a thermal equilibrium;

selecting a point C and a point D on the second one-dimensional structure on the same side of the suspended junction, detecting and calculating a first frequency difference $\Delta Y_{OC}$ of Raman spectrum characteristic peaks between the suspended junction and the point C, and detecting and calculating a second frequency difference $\Delta Y_{CD}$ of Raman spectrum characteristic peaks between the point C and the point D, wherein the suspended junction, the point C and the point D are spaced equidistantly with a distance $\Delta x$;

calculating a first temperature difference $\Delta T_{OC}$ between the suspended junction and the point C and calculating a second temperature difference $\Delta T_D$ between the point C and the point D by a formula $\Delta T = \Delta Y/a$, wherein the $\Delta T$ represents a temperature difference between two spaced points, and the $\Delta Y$ represents a frequency difference between the two spaced points, and 'a' is constant;

calculating a third temperature difference $\Delta T_j$ between the first one-dimensional structure and the second one-dimensional structure at the suspended junction by a formula $\Delta T_j = \Delta T_{OC} - \Delta T_{CD}$;

calculating a heat flux $Q_j$ by a formula $Q_j = 2k\Delta T_{CD}/\Delta x$, wherein the $Q_j$ represents the heat flux flowing from the first one-dimensional structure to the second one-dimensional structure through the suspended junction, and the k represents a thermal conductivity of the first one-dimensional structure; and calculating a contacting thermal resistance $R_j$ by a formula $R_j = \Delta T_j/Q_j$, wherein the $R_j$ represents the contacting thermal resistance between the first one-dimensional structure and the second one-dimensional structure at the suspended junction.

13. The method of claim 12, wherein both the first one-dimensional structure and the second one-dimensional structure have an effective diameters in a range from about 0.5 nanometers to about 100 nanometers.

14. The method of claim 13, wherein both the first one-dimensional structure and the second one-dimensional structure are nanotubes, nanorods, nanowires, nanofibers, or nanoribbons.

15. The method of claim 14, wherein the first one-dimensional structure and the second one-dimensional structure are two single wall carbon nanotubes.

* * * * *